United States Patent [19]

Lambrecht et al.

[11] 4,409,966
[45] Oct. 18, 1983

[54] METHOD AND APPARATUS FOR INJECTING A SUBSTANCE INTO THE BLOODSTREAM OF A SUBJECT

[75] Inventors: Richard M. Lambrecht, Quogue; Gerald W. Bennett, East Moriches, both of N.Y.; Charles C. Duncan, New Haven, Conn.; Louis W. Ducote, Shoreham, N.Y.

[73] Assignee: The United States of America as represented by the U.S. Department of Energy, Washington, D.C.

[21] Appl. No.: 268,423

[22] Filed: May 29, 1981

[51] Int. Cl.$^3$ .............................................. A61B 6/00
[52] U.S. Cl. ...................................... 128/1.1; 604/50; 604/66
[58] Field of Search ...................... 128/1.1, 1.2, 214 E; 604/27, 31, 50, 65, 66, 67

[56] References Cited

U.S. PATENT DOCUMENTS 3,847,138 11/1974 Gollub .................................. 128/1.1
4,224,303 9/1980 Shaw ..................................... 128/1.2
4,294,248 10/1981 de Figueiredo ................. 128/214 E Primary Examiner—Richard J. Apley
Assistant Examiner—George Yanulis
Attorney, Agent, or Firm—Margaret C. Bogosian; Paul A. Gottlieb; Richard G. Besha

[57] ABSTRACT

An apparatus and method for injecting a substance, such as a radiopharmaceutical, into the bloodstream of a subject. The apparatus comprises an injection means, such as a servo controlled syringe, a means for measuring the concentration of that substance in the subject's bloodstream, and means for controlling the injection in response to the measurement so that the concentration of the substance follows a predetermined function of time. The apparatus of the subject invention functions to inject a substance into a subject's bloodstream at a rate controlled by an error signal proportional to the difference between the concentration of the substance in the subject's bloodstream and the predetermined function.

8 Claims, 2 Drawing Figures

METHOD AND APPARATUS FOR INJECTING A SUBSTANCE INTO THE BLOODSTREAM OF A SUBJECT

BACKGROUND OF THE INVENTION

The U.S. Government has rights in this invention pursuant to Contract Number DE-AC02-76CH00016, between the U.S. Department of Energy and Associated Universities, Inc.

This invention relates to the use of radiopharmaceuticals in the study of metabolic processes, and in particular, to a method and apparatus for the injection of substances, such as radiopharmaceuticals, into the bloodstrem of a subject.

The use of radiopharmaceuticals has become an important tool in the study of physiological processes. If radiopharmaceuticals are given to a subject their progress through the body may be traced by detecting their radiation as the active elements in the radiopharmaceuticals decay.

A particularly interesting subject of study is the study of blood flow, and particularly, the study of regional cerebral blood flow, (i.e., the blood flow in particular regions of the brain) through the use of the technique of positron emission tomography. In these studies a positron emitting radiopharmaceutical is injected into the subject's blood stream. When a positron is emitted from the radiopharmaceutical it is almost instantaneously annihilated by an encounter with an electron, resulting in the emission of two gamma rays at an angle of 180° with respect to each other. By placing two detectors in line on opposite sides of the region of the subject's brain under study and looking for near simultaneous detection of gamma rays in each detector, it is possible to detect the presence of a positron emitting radiopharmaceutical with high accuracy. By slowly rotating a pair of detectors, or providing a number of detector pairs at various angles around the subject, it is possible to form an image of the region under study by the mathematical technique, which is well known to those skilled in the art, of tomography. Devices for performing this sort of measurement are commercially available and are commonly known as PET scanners. (Further details of positron emission tomography and PET scanners are well known to those skilled in the art and are not necessary for an understanding of the present invention and will not be described further here.)

In the past, blood flow studies using radiopharmaceuticals have been performed by injecting the radiopharmaceutical into the subject's blood stream, either essentially all at once, or at best at a uniform rate over a period of time. A problem with this prior technique is that since a concentration of the radiopharmaceutical in the blood stream changes, both due to the natural radioactive decay of the radiopharmaceutical and due to the metabolic elimination of the radiopharmaceutical from the body, it is not possible to know the concentration of the radiopharmaceutical in the blood stream at any time. This is particularly important in the studies of regional cerebral blood flow described above, since blood perfuses through the brain at different rates in different regions, and considerable time is needed to perform a PET scan. To compensate for these differences, it is necessary to provide radiopharmaceuticals in such a manner that its concentration in the blood stream increases linearly over a period of time.

Thus, it is an object of the present invention to provide a method and apparatus for the injection of a substance, such as radiopharmaceuticals, into the blood stream of a subject so that the concentration of said substance is a predetermined function of time.

It is a further object of the present invention to provide a method and apparatus for the injection of a radiopharmaceutical into the blood stream where a concentration increases linearly over a predetermined period of time.

It is a still further object of the present invention to provide a method and apparatus for the injection of radiopharmaceuticals into a subject's blood stream which is useful in the study of regional cerebral blood flow.

It is yet further an object of the present invention to provide a method and apparatus for the injection of radiopharmaceuticals into a subject's blood stream which is useful in conjunction with the technique of positron emission tomography.

BRIEF SUMMARY OF THE INVENTION

The above objects are achieved and the disadvantages of the prior art overcome by means of the present invention, which comprises a means, such as a motor driven syringe, for injecting a substance, such as a radiopharmaceutical, into the blood stream of the subject, and means for measuring the concentration of said substance in the subject's blood stream. This measurement may be made most simply by measuring the level of activity due to said substance, where said substance is a radiopharmaceutical, in a small fixed volume of the subject's blood stream, but other methods for making these measurements are within the contemplation of the present invention provided only that they may be carried out in a time that is short compared to the radioactive and biological-lives of said substance. (By radioactive half-life herein is meant the amount of time required for one-half the original amount of substance to decay, and by biological half-life herein is meant the amount of time required for biological processes to remove one-half the original amount of substance from the subject's blood stream). For example, by using spectrographic techniques to measure fluorescence or light absorption the method and apparatus of the present invention may also be adapted for use with non-radioactive substances.

The present invention further comprises means for generating a function of the time elapsed after the beginning of the injection of said substance, said function serving as a reference for the desired concentration of said radiopharmaceutical in the subject's blood stream, and means for comparing the concentration in the subject's blood stream with said function, and generating an error signal proportional to the variation of said concentration from said function. The present invention also comprises means for controlling the rate of injection by said injection means in response to said error signal.

It will be obvious to those skilled in the art that the above described apparatus functions to inject a substance into a subject's blood stream at a rate proportional to an error signal which is generated by the comparison of a predetermined function with the concentration of said substance in the subject's blood stream.

Thus, the present invention advantageously provides a means for injecting a radiopharmaceutical into a subject's blood stream so that the concentration of said radiopharmaceutical is a predetermined function of time.

Other objects and advantages of the present invention will be readily apparent to those skilled in the art from an examination of the drawings and consideration of the detailed description set forth below.

DETAILED DESCRIPTION OF A PREFERRED EMBODIMENT OF THE INVENTION

Figure 1:
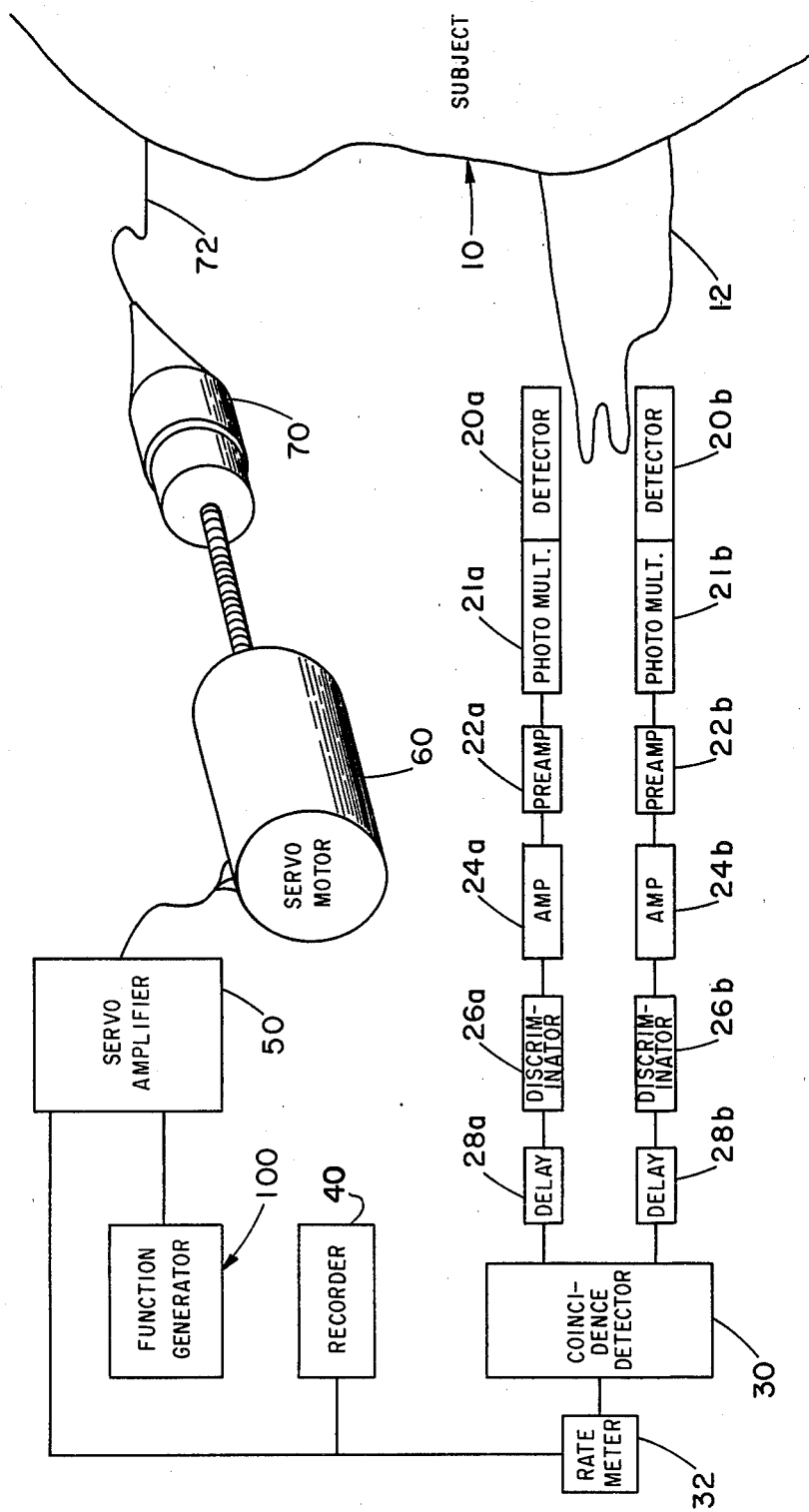
FIG. 1 is a schematic block diagram of the system in accordance with the present invention.

Turning now to FIG. 1, there is shown a schematic representation of an embodiment of the present invention suitable for the injection of a radiopharmaceutical.

A shunt 12 is implanted in a subject 10, so that a portion of arterial blood flow may be routed outside the body of the subject and returned to a vein. Implanting shunt 12 is a minor surgical procedure which might be performed by any medical doctor or, if the subject is not human, by any person with some surgical skill and experience in animal experimentation. Alternatively, a distal portion of an extremity may be placed between the detectors for a less invasive procedure.

The radiopharmaceutical is placed in automatic syringe 70, which is driven by servo motor 60, and connected to a vein in the subject by catheter 72. The connection of catheter 72 is an even more minor surgical procedure, which might be carried out by any of the persons described above.

Shunt 12 is positioned between NaI(T1) (sodium iodide thermoluminesent) detectors 20a and 20b, which are positioned on opposite sides of shunt 12 to detect the coincident gamma ray pair created by the positron/electron annihilation. The outputs of detectors 20a and 20b, which are light pulses, are converted to electrical signals by photomultipliers 21a and 21b and preamps 22a and 22b and amplified by amplifiers 24a and 24b. The output of amplifiers of 24a and 24b is a pulse whose height is proportional to the energy of the gamma ray detected by detectors 20a and 20b. This output goes to discriminators 26a and 26b, which are preset to produce an output pulse only for inputs corresponding to the appropriate gamma ray energy for positron/electron annihilation. These pulses pass through variable delays 28a and 28b, to coincidence detector 30. Coincidence detector 30 produces an output only when two pulses reach it essentially simultaneously, and delays 28a and 28b are adjusted so that the total delay through each of the channels described is essentially equal. Thus, the output of coincidence detector 30 is a pulse stream whose average rate is proportional to the rate of positron/electron annihilations, which in turn is proportional to the radiopharmaceutical concentration in the subject's blood stream.

It should be noted that while the use of coincidence detection as described above minimizes the need for shielding detectors 20a and 20b to reduce background radiation, there is in principle no reason why a single channel as described above with a properly shielded detector, and in particular, a detector well shielded from the body of subject 10, could not be used.

The output of coincidence detector 30 is connected to rate meter 32, which converts the average pulse rate in coincidence detector 30 into a continuous electrical signal which is connected to servo amplifier 50 and recorder 40.

Generator 100, which will be described more fully below, is connected to the other input servo amplifier 50. In the embodiment shown the output of function generator 100 is a linearly increasing ramp which ranges from 0 to full scale in a predetermined period of time. The output of servo amplifier 50 is an error signal, proportional to the difference between the output of rate meter 32 and the output of function generator 100, which controls servo motor 60 so as to increase or decrease the rate of injection from syringe 70 into subject 10, so that the concentration of radiopharmaceutical in the blood stream of subject 10 tracks the output of function generator 100 and is a linearly increasing function of time.

While in the embodiment shown the concentration of radiopharmaceutical is a linearly increasing function, it is within the contemplation of the present invention to provide for other concentration functions. For example, in the study of blood flow in the heart, it may be desirable to maintain the concentration of the blood stream at a constant level or at an exponentially changing level.

It should be noted that each of the subsystems described above, with the exception of function generator 100, which will be more fully described below, is a conventional, commercially available, apparatus. Details of their use, interconnection, and the provision of power for these subsystems are well known to those skilled in the art and need not be described further here for an understanding of the invention.

Figure 2:
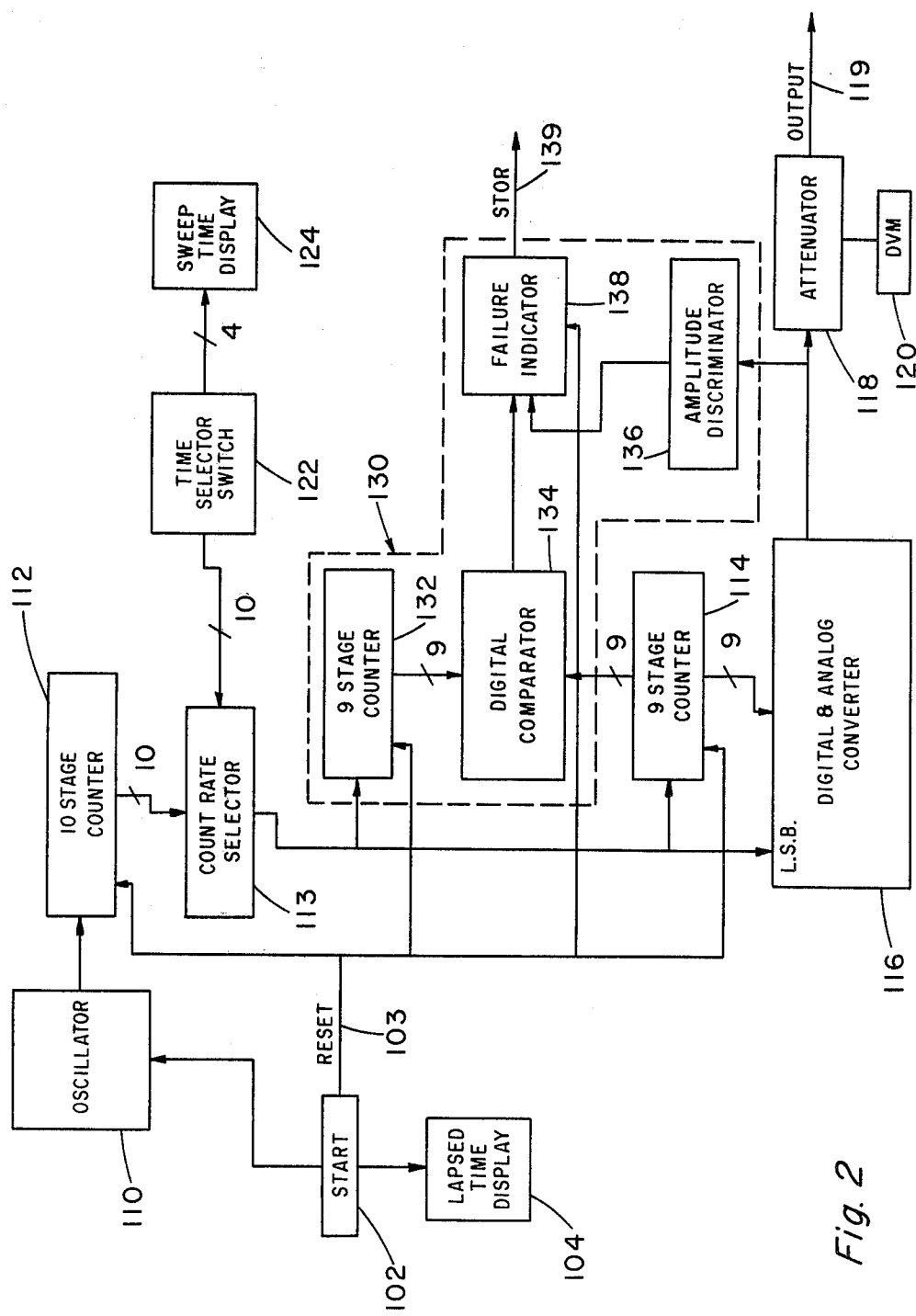
FIG. 2 is a schematic block diagram of a circuit for generating a linearly increasing signal for a predetermined period of time to be used in the apparatus shown in FIG. 1.

Turning now to FIG. 2, there is shown a schematic block diagram of function generator 100 in accordance with the present invention which provides an output reference signal which increases linearly from 0 to full scale at a preselected rate.

A start signal is provided from a conventional switch 102, or other similar means, such as a relay. Coincidentally with the start signal, a reset pulse will be provided on reset line 103 to set function generator 100, to an initial state. The start signal will complete a circuit electrically connecting oscillator 110, which will typically operate at a frequency in excess of 100,000 Hz± approximately 0.01% and start lapsed time display 104. The operating frequency is then frequency divided down to an output frequency of about 20 Hz, which is connected to ten-stage binary counter 112. At each successive stage of counter 112 the frequency is divided by a factor of 2 (i.e., at the output of the first stage the frequency is 10 Hz, at the second 5 Hz, etc.). The output of each of the stages of counter 112 is connected to an input of count rate selector 113. The output of count rate selector 113 is one of the ten frequencies produced by counter 112 and selected by setting sweep time selector switch 122. Sweep time selector switch 122 is also connected to sweep time display 124, to display the selected sweep time. The output of count rate selector 113 is connected to the input of binary counter 114 and to the least significant bit of digital-to-analog converter 116. The nine stages of counter 114 are sequentially connected to the remaining nine inputs of digital-to-analog converter 116. Thus, the output of digital-to-analog converter 116 increases by a fixed amount each time counter 114 is incremented to form a staircase approximation of a linearly increasing function ranging from 0 to approximately 10 volts. The duration of this function is determined by the output of count rate selector 113, and ranges from a minimum of approximately one minute forty-two seconds, to a maximum of approximately fourteen hours and thirty-two minutes in ten steps, each step being twice as long as the preceding step. The output of digital-to-analog converter 116 is attenuated by attenuator 118 to a range of from 0 to about one volt, so as to be compatible with servo amplifier 50. The attenuated output is connected to servo amplifier 50 on line 119 and is also displayed on digital volt meter 120.

One possible hazard associated with the apparatus shown in FIG. 1 is that a failure in the function generator 100 might cause a sudden large change in the output of digital-to-analog converter 116. If servo amplifier 50 were to follow this erroneous output, the sudden increase in the injection rate would cause a hydrostatic shock in the blood stream of subject 10, with possibly serious harmful effects. To prevent this, safety circuit 130 is incorporated into function generator 100.

Safety circuit 130 comprises a second nine stage binary counter 132, which is also connected to the output count rate selector 113. The states of counters 132 and 114 are compared by digital comparator 134, whose output is connected to failure indicator 138. In the event that counters 132 and 114 do not compare, failure indicator 138 shows a failure and outputs a stop signal on line 139 to servo amplifier 50 to stop servo motor 60. Additionally, amplitude discriminator 136 is connected to the output of digital-to-analog converter 116, and the output of amplitude discriminator 136 is also connected to failure indicator 138. Amplitude discriminator 136 produces an output if there is a sudden sharp change in the output of digital-to-analogue converter 116, which exceeds a certain preselected magnitude. Thus, failure circuit 130 will prevent servo amplifier 50 from trying to follow sudden sharp changes in the output of function generator 100.

After reviewing the above disclosure and with an understanding of the function and purpose of the subject invention the design and interconnection of each of the circuits described above in function generator 100 would be apparent to a person skilled in the art, or would be within the routine skills of an electronics technician familiar with digital circuitry and no further description of the construction for operation of function generator 100 is believed necessary for the understanding of the present invention.

EXPERIMENTAL EXAMPLE I

The following experiment was conducted to demonstrate the utility of the present invention. An apparatus essentially as shown in FIG. 1, and described above, was constructed.

3.7 Millicuries of fluorine-18 labeled 4-fluoroantipyrene was dissolved in 10 milliliters of isotonic saline solution, and was contained in a 10 cc syringe for injection into a 3.25 kg female cat. (Fluorine-18 is a radionuclide with a half-life of 110 minutes, which decays by positron emission.) was maintained under anesthesia under physiologically controlled conditions. The head of the animal was positioned in the PETT III positron emission tomograph, such that the blood flow in the brain could be studied. The solution was injected over a period of approximately 54 minutes under the control of the injection control system of the present invention. The arterial concentration of fluorine-18 was recorded and was found to increase linearly over the 54 minute period.

The physiological state of the animal was altered by increasing partial pressure of carbon dioxide in the arterial blood flow at discrete times during the injection. An increase in $CO_2$ pressure should increase the rate of cerebral blood flow and a change in cerebral blood flow was detected with a PETT III tomograph. This experiment demonstrated that a linearly increasing concentration of the radiopharmaceutical could be maintained for an extended period in an animal under physiologically altered conditions.

The above description and examples and the attached drawings are set forth by way of illustration only, and many other embodiments of the present invention will be apparent to those skilled in the art. Limitations on the present invention are only to be found in the claims set forth below.

What is claimed is:

1. A method for injecting a radiopharmaceutical into the blood stream of a subject, so that a concentration of said radiopharmaceutical in the blood stream of said subject increases linearly over a period of time making said concentration follow a predetermined function of time, comprising the steps of:
   (a) injecting said radiopharmaceutical into the blood stream of said subject;
   (b) measuring for the concentration of said radiopharmaceutical in the blood stream of said subject; and
   (c) controlling the rate of said injection in response to said measurement so as to cause the concentration of said radiopharmaceutical in the blood stream of said subject increases linearly over a period of time making said concentration follow a predetermined function of the time elapsed since the beginning of the injection.

2. The method of claim 1, wherein said measurement is made by determining the activity of said radiopharmaceutical in a predetermined volume of the arterial blood flow of said subject.

3. A method as described in claim 1, wherein the concentration of said radiopharmaceutical in the blood stream of said subject increases linearly for a predetermined period of time.

4. A method of injecting a substance into the blood stream of a subject, so that a concentration of said substance in the blood stream of said subject increases linearly with time making said concentration follow a predetermined function of time, comprising the steps of:
   (a) providing a signal proportional to the concentration of said substance in the blood stream of said subject;
   (b) connecting said signal into a feedback loop to control the rate of injection of said substance; and,
   (c) injecting said substance at said controlled rate.

5. A method as described in claim 4, wherein said substance is a radiopharmaceutical and said signal is provided by measuring the activity of said radiopharmaceutical in a predetermined volume of the arterial blood flow of said subject.

6. An apparatus for the injection of a radiopharmaceutical into the bloodstream of a subject, such that the concentration of said radiopharmaceutical in the bloodstream increases linearly over a period of time making said concentration a predetermined function of time and thus a known quantity for any given time, comprising:

(a) means for the injection of said radiopharmaceutical into the bloodstream of said subject, said injection means being driven by a servo motor;
(b) means for measuring the concentration of said radiopharmaceutical in the bloodstream of said subject that permits this measurement to be carried out in a time that is short compared to the radioactive and biological-lives of said radiopharmaceutical;
(c) means for generating a function of the time elapsed after the beginning of the injection of said radiopharmaceutical, which function reflects the half-life of said radiopharmaceutical and the physiological parameters effecting disposition of said radiopharmaceutical, said function serving as a reference for the desired concentration of said radiopharmaceutical in the bloodstream of said subject;
(d) means for comparing the concentration of said radiopharmaceutical in the bloodstream of said subject with said function and generating an error signal proportional to the variation of said concentration from said function; and
(e) means for controlling the rate of injection by said injection means in response to said error signal.

7. An apparatus as described in claim 6, wherein said radiopharmaceutical is a positron emitting radiopharmaceutical and said measuring means measures the activity of said radiopharmaceutical in a predetermined volume of the arterial blood flow of said subject by coincidentally detecting the gamma rays emitted in opposite directions by positron/electron annihilation.

8. An apparatus as described in claim 6 wherein:
(a) said injection means comprises an automatic syringe driven by said servo motor;
(b) said comparison means further comprises a servo amplifier means, connected to said function generator and to said measuring means, for producing an error signal, said error signal being proportional to the difference between the signals from said function generator and said measuring means; and
(c) said injection control means controls said servo motor to vary the rate of injection of said radiopharmaceutical.

* * * * *